United States Patent
Gong et al.

(10) Patent No.: US 10,987,655 B2
(45) Date of Patent: Apr. 27, 2021

(54) MOLYBDENUM-VANADIUM BIMETALLIC OXIDE CATALYST AND ITS APPLICATION IN CHEMICAL LOOPING OXIDATIVE DEHYDROGENATION OF ALKANE

(71) Applicant: TIANJIN UNIVERSITY, Tianjin (CN)

(72) Inventors: Jinlong Gong, Tianjin (CN); Sai Chen, Tianjin (CN); Liang Zeng, Tianjin (CN); Rentao Mu, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 16/605,504

(22) PCT Filed: Jul. 25, 2018

(86) PCT No.: PCT/CN2018/096942
§ 371 (c)(1),
(2) Date: Oct. 16, 2019

(87) PCT Pub. No.: WO2019/029358
PCT Pub. Date: Feb. 14, 2019

(65) Prior Publication Data
US 2020/0122121 A1  Apr. 23, 2020

(30) Foreign Application Priority Data
Aug. 8, 2017  (CN) .......................... 201710672211.3

(51) Int. Cl.
*C07C 5/32* (2006.01)
*B01J 23/28* (2006.01)
(Continued)

(52) U.S. Cl.
CPC ............... *B01J 23/28* (2013.01); *B01J 6/001* (2013.01); *B01J 37/0201* (2013.01);
(Continued)

(58) Field of Classification Search
None
See application file for complete search history.

(56) References Cited

U.S. PATENT DOCUMENTS

| | | | | |
|---|---|---|---|---|
| 4,925,825 A | * | 5/1990 | Tachi ................. | B01D 53/8628 502/309 |
| 6,521,808 B1 | * | 2/2003 | Ozkan ................. | C07C 5/3332 585/661 |

(Continued)

OTHER PUBLICATIONS

Liang-Shin Fan, et al. Chemical Looping Processes for CO2 Capture and Carbonaceous Fuel Conversion-Prospect and Opportunity. Energy&Environmental Science, 2012, 5(6), 7254-7280.
(Continued)

*Primary Examiner* — Philip Y Louie
(74) *Attorney, Agent, or Firm* — Bayramoglu Law Offices LLC

(57) ABSTRACT

A molybdenum-vanadium bimetal oxide catalyst having a molecular formula of $Mo_1V_y$, where y represents an atomic molar ratio of vanadium and molybdenum. An oxygen support $Mo_1V_y$ is prepared by an impregnation method including impregnation, drying, calcination, and tablet pressing. In the dehydrogenation reaction of a light alkane to an alkene over the supported molybdenum-vanadium bimetal oxide, the reaction temperature is 450° C.-550° C. Propane can be oxidized and dehydrogenated to produce propylene with a high activity and high selectivity. A conversion rate of propane remains at 30%-40%, and a selectivity for propylene is 80%-90%. A fresh oxygen support changes from a high-valence state to a low-valence state after reacting with propane. A low-valence state oxygen support reacts with air or oxygen to be oxidized to a high-valence state, and recovers lattice oxygen and cycles again.

8 Claims, 6 Drawing Sheets

(51) Int. Cl.
  *B01J 23/22* (2006.01)
  *B01J 6/00* (2006.01)
  *B01J 37/02* (2006.01)
  *B01J 21/04* (2006.01)
  *B01J 21/06* (2006.01)
  *B01J 21/08* (2006.01)

(52) U.S. Cl.
  CPC ............... *C07C 5/322* (2013.01); *B01J 21/04* (2013.01); *B01J 21/063* (2013.01); *B01J 21/08* (2013.01); *B01J 2208/028* (2013.01); *C07C 2523/28* (2013.01)

(56) References Cited

U.S. PATENT DOCUMENTS

2003/0181325 A1\* 9/2003 Ou ........................ B01J 23/34
  502/302
2010/0000410 A1\* 1/2010 Nagai ..................... B01J 23/30
  95/283
2017/0334808 A1\* 11/2017 Huang ................... C07C 5/3337
2017/0354955 A1\* 12/2017 Hossain .................... C07C 5/48

OTHER PUBLICATIONS

Yu, Xiaochuan, Study on the Active Sites of Supported Vanadium-Based Catalysts in Oxidative Dehydrogenation of Propane. China Master's Theses Full-Text Database, Oct. 31, 2009.

Viviana Murgia, et al. Influence of Concentration and Order of Aggregation of the Active Phases in V—Mo—O Catalysts in the Oxidative Dehydrogenation of Propane. Catalysis Today, No. 133-135, Mar. 5, 2008, pp. 87-91.

Miguel A. Banares, et al. Structure-Activity Relationships in Alumina-Supported Molybdena-Vanadia Catalysts for Propane Oxidative Dehydrogenation, Catalysis Today, No. 96, Aug. 24, 2004, pp. 251-257.

\* cited by examiner

MOLYBDENUM-VANADIUM BIMETALLIC OXIDE CATALYST AND ITS APPLICATION IN CHEMICAL LOOPING OXIDATIVE DEHYDROGENATION OF ALKANE

CROSS REFERENCE TO THE RELATED APPLICATIONS

This application is the national phase entry of International Application No. PCT/CN2018/096942, filed on Jul. 25, 2018, which is based upon and claims priority to Chinese Patent Application No. 201710672211.3, filed on Aug. 8, 2017, the entire contents of which are incorporated herein by reference.

TECHNICAL FIELD

The present disclosure relates to a dehydrogenation technology of light alkanes over a metal oxide. More specifically, the present disclosure relates to an application of oxidative dehydrogenation of a light alkane to prepare an alkene over a supported molybdenum-vanadium bimetal oxide, and a method thereof.

BACKGROUND

Shale gas is an important and unconventional natural gas resource that is rich in light alkanes. The conversion of light alkanes in shale gas for more valuable chemical products is crucial for the environment. In recent years, alkanes dehydrogenation technology has progressed.

For example, the conventional non-oxidative dehydrogenation technology for propane dehydrogenation (PDH) for preparing propylene uses a Pt-based or Cr-based catalyst, and the PDH reaction has a high selectivity for propylene under the Pt-based catalyst condition. However, since the PDH reaction is subjected to thermodynamic limits, the single-pass conversion rate cannot be effectively improved. Moreover, non-oxidative dehydrogenation is an endothermic reaction, which consumes a large amount of energy in the reaction stage. Although the Cr-based catalyst has solved the cost issue of the Pt-based catalyst, Cr is highly toxic to people and the environment, and the thermodynamic limits are still an issue. Therefore, an economical and efficient method for producing propylene from propane is imperative. Oxidative dehydrogenation (ODH) is a potential dehydrogenation method, which introduces molecular oxygen into the reaction system, and breaks the thermodynamic limits. Propane and propylene are likely to conduct a complete oxidation reaction to generate $CO_2$ when in the presence of molecular oxygen, which affects the selectivity and cost of the method. The reaction condition of the reducing gas mixed with the oxygen is requires a strict control but also creates many safety concerns. Therefore, it is difficult to use the ODH method in a wide scale in the industry.

Chemical looping technology is able to achieve a near-zero-energy in-situ separation of products during the fuel conversion. Such an advanced and an efficient thermochemical technology has generated extensive attention. [Fan L-S, Zeng L, Wang W, Luo S. Chemical looping processes for $CO_2$ capture and carbonaceous fuel conversion—prospect and opportunity [J]. Energy & Environmental Science, 2012, 5 (6), 7254-7280.]. Chemical looping oxidative dehydrogenation (CL-ODH) refers to activate propane with a high selectivity to produce propylene by using lattice oxygen in a metal oxide (oxygen support), which not only overcomes the influence of thermodynamic limits in non-oxidative dehydrogenation, but also prevents propane from being deeply oxidized with propylene in the presence of molecular oxygen. A device and a process of CL-ODH of propane are shown in FIG. 1. A metal oxide catalyst is provided in a fixed bed reactor. A gas switch device is arranged in a gas inlet path. The gas switch device is connected to a raw material gas path, an inert gas path and an oxidizing gas path, and can be switched to allow the gas inlet path to connect to the raw material gas path, the inert gas path, and the oxidizing gas path, respectively. The raw material gas path is configured to introduce a raw material light alkane to the fixed bed reactor. The inert gas path is configured to purge inert atmosphere into the gas inlet path and the fixed bed reactor, so that the reaction can be performed under an anaerobic condition. The oxidizing gas path is configured to supply oxygen or air to the fixed bed reactor, so as to oxidize and regenerate the metal oxide catalyst. When the device is in use, the inert gas path, the gas inlet path, and the fixed bed reactor are connected to a gas outlet pipe, so as to eliminate oxygen in the entire reaction system. Then, a switch to the raw material gas path is performed to introduce the raw material light alkane into the fixed bed reactor for reaction. The activity of the metal oxide catalyst during the reaction is monitored, e.g. product compositions, reaction time, metal oxide valence states, and other parameters. When the activity of the metal oxide catalyst is close to the limit, a switch to the oxidizing gas path is performed to introduce oxygen or air, so as to oxidize and regenerate the metal oxide catalyst from a low-valent state to a high-valence state. After the regeneration, a switch to the inert gas path is performed to remove oxygen, a switch to the raw material gas path is performed for the reaction, and another switch to the oxidizing gas path is performed for regeneration. A reaction system consisting of two or more fixed bed reactors is employed to ensure that at least one fixed bed reactor is in the reaction stage at any time while the remaining fixed bed reactors are in the regeneration stage or deoxygenation stage, thereby realizing a continuous production of the entire reaction process.

At present, the oxygen supports used in CL-ODH are mainly single-component metal oxides, e.g. vanadium oxide, chromic oxide, tungsten oxide, and others. However, the activity of lattice oxygen of these single-component metal oxides is affected by many factors due to their own crystal structures, which cannot efficiently activate the carbon-hydrogen bond of propane with a high activity and selectivity to produce propylene. Therefore, effectively regulating the activity of lattice oxygen by constructing a composite metal oxide has important scientific and economic benefits. In the previous research, we applied for a catalyst for alkane dehydrogenation and a reaction device for a fixed bed, a moving bed, and a circulating fluidized bed. The catalyst in the present disclosure is a non-precious metal, which is non-toxic and can be continuously reacted and regenerated in a reactor matched with the catalyst. Even so, the selectivity of the catalyst needs to be further improved while maintaining the high catalytic activity.

SUMMARY

The objective of the present disclosure is to overcome the drawbacks of thermodynamic limits, low selectivity for propylene, low economic efficiency of the reaction in the prior art, and to provide a molybdenum-vanadium bimetal oxide catalyst and an application in chemical looping oxidative dehydrogenation of the light alkane thereof. The molybdenum-vanadium bimetal oxide catalyst is used as an oxygen support. Lattice oxygen in the oxygen support reacts with the hydrogen atom in the activated propane to generate water, which effectively promotes the reaction to move in the direction of producing propylene. Compared with single vanadium oxide, the addition of Mo significantly inhibits the surface oxygen activity, and the conversion rate of propane and the selectivity for propylene are remarkably improved, which effectively improves the propylene yield and the efficiency of the reaction.

The objective of the present disclosure is realized by the following technical solutions.

The molybdenum-vanadium bimetal oxide catalyst is a solid solution formed by an oxide of molybdenum (Mo) and an oxide of vanadium (V). The molar ratio of Mo and V is 1:(4-30), and preferably 1:(6-18).

Mo enters the bulk phase lattice of $V_2O_5$, resulting in a lattice distortion of $V_2O_5$ and forming a molybdenum-vanadium solid solution.

The catalyst is a supported catalyst, and the support is $Al_2O_3$, $TiO_2$, $SiO_2$ or a molecular sieve. The mass percent of the oxide of molybdenum (i.e., mass of the oxide of molybdenum/mass of the support) is 1%-30%, and preferably 10%-20%. The mass percent of the oxide of vanadium (i.e., mass of the oxide of vanadium/mass of the support) is 4%-60%, and preferably 40%-60%.

During the preparation of the alkene, the following steps are performed:

step 1, uniformly dispersing ammonium metavanadate and oxalic acid in deionized water, adding ammonium molybdate according to an atomic ratio of molybdenum and vanadium, and uniformity mixing to form an impregnating solution.

step 2, placing the support in the impregnating solution prepared in step 1 and performing an equal-volume impregnation on the support;

step 3, drying the support impregnated in step 2 at a room temperature of 20° C.-25° C. for 8 h-12 h, then, drying the support at 70° C.-90° C. for 8 h-12 h, and finally, calcining the support at 550° C.-600° C. for 2 h-4 h under air atmosphere, to obtain the molybdenum-vanadium bimetal oxide catalyst, wherein the molecular formula thereof is $Mo_1V_y$, and y represents an amount of V corresponding to 1 mol of Mo, i.e. a molar ratio of V to Mo.

In step 1, the mass ratio of oxalic acid to ammonium metavanadate is (2.8-3):(1.5-2).

In step 2, the support is $Al_2O_3$, $TiO_2$, $SiO_2$ or a molecular sieve.

In step 3, drying the support at the room temperature of 20° C.-25° C. for 10 h-12 h, then drying the support at 80° C.-90° C. for 10 h-12 h, and finally calcining the support at 550° C.-600° C. under air atmosphere for 2 h-4 h.

In step 3, molybdenum-vanadium bimetal oxide catalyst powder is pressed into a granular catalyst with the size of 20-40 mesh.

The catalyst of the present invention is applied to chemical looping oxidative dehydrogenation of a light alkane, and the reaction is performed under an anaerobic condition. The catalysts is used as an oxygen support, and reacts with the light alkane via oxidative dehydrogenation. The lattice oxygen in the oxygen support is combined with the hydrogen atom in the light alkane to form water, the oxygen support is reduced to a low-valence state, and the light alkane is oxidized to the corresponding alkene.

The light alkane is an alkane having at least one carbon atom, and preferably includes a linear chain alkane having one carbon atom. Most preferably, the alkane is one selected from the group consisting of ethane, propane, n-butane, and iso-butane.

The lattice oxygen in the catalyst participates in the reaction. Therefore, the lattice oxygen is gradually consumed as the reaction proceeds, resulting in a decrease in the catalyst activity. So, the catalyst needs to be cycled and regenerated. The low valence-state oxygen support reacts with air or oxygen and is oxidized to a high-valence state, recovering the lattice oxygen, and then returns to the reactor for reaction.

In the oxidative dehydrogenation reaction, the gas-solid two-phase (the gas phase mainly includes the raw material light alkane and the product light alkene, and the solid phase mainly includes the metal oxide oxygen support) contacting methods mainly include two contacting methods of a gas-solid countercurrent contacting method and a gas-solid co-current contacting method. Specifically, a fixed bed reactor, a moving bed reactor or a circulating fluidized bed is employed.

During use, the catalyst is uniformly mixed with quartz sand, and the reaction is performed under a normal pressure. The reaction temperature is 450° C.-500° C. Nitrogen is introduced to remove oxygen and air, and then propane is introduced. The total flow of propane and nitrogen is 20 ml/min-50 ml/min, and the volume percent of propane is 10%-30%. The mass ratio of catalyst to quartz sand is (0.2-1):1, preferably (0.5-0.8):1.

Compared with the present dehydrogenation techniques, the present invention has the following advantages.

(1) The present invention provides a supported bimetal oxide, which is a bimetal composite oxide formed by vanadium oxide and molybdenum oxide. Compared with the single vanadium oxide, the selectivity for light alkene is obviously improved. Compared with the single molybdenum oxide, the conversion rate of light alkane is increased. The optimal values of the conversion rate and the selectivity can be obtained by adjusting the ratio of molybdenum to vanadium.

(2) The impregnation method for preparing the oxygen support of the present invention is convenient to operate and is cost-effective.

(3) The oxygen support can maintain a high conversion rate and a high selectivity after the lattice oxygen is consumed.

(4) After the oxygen support undergoes several redox regeneration cycles, the oxygen support basically maintains a stable structure and performance, and the conversion rate and the selectivity remain basically unchanged.

(5) Oxygen or air needs to be introduced during the regeneration stage of the catalyst, so that the oxygen support can be oxidized to supply lattice oxygen. Moreover, the oxidation of the oxygen support is an exothermic reaction. With the combustion of deposited carbon, the released heat can enter the reactor to supply heat to the dehydrogenation reaction via the heat conduction effect of the oxygen support. An exact matching of heat can be achieved by adjusting the mass of the oxygen support.

(6) The catalyst of alkane dehydrogenation of the present invention is applied to a chemical looping oxidative dehydrogenation reaction device. Compared with the prior art, the present invention has the advantages of high single-pass conversion rate of the alkane, high selectivity for the target product alkene, and the active ingredient of the catalyst is a non-precious metal. Moreover, there is no introduction of sulfide medium, and no negative influence on the environment.

DETAILED DESCRIPTION OF THE EMBODIMENTS

Figure 1:
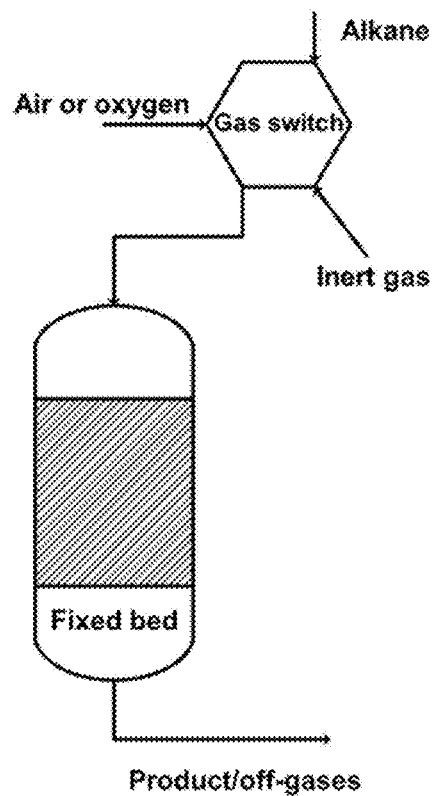
FIG. 1 is a schematic diagram showing a device and a chemical looping oxidative dehydrogenation process of propane of the present invention.

The technical solution of the present disclosure is further described hereinafter with reference to the embodiments.

Firstly, a Mo—V bimetal oxide catalyst is prepared. Each part by mass is 1 g. Meanwhile, the single metal oxide catalysts of V and Mo are prepared, which are used for the comparison and verification. The three metal oxide catalysts are prepared by the same preparation process parameters.

Embodiment 1

Step 1, 1.8 parts by mass of ammonium metavanadate ($NH_4VO_3$) and 2.9 parts by mass of oxalic acid ($C_2H_2O_4$) are weighed and dissolved in 3 mL of deionized water. After the reaction is completed, a certain mass of ammonium molybdate (($NH_4)_6Mo_7O_{24} \cdot 4H_2O$) is added according to the atomic ratio of molybdenum and vanadium, and 2.0 parts by mass of $Al_2O_3$ are added in the above-mentioned solution.

Step 2, the product obtained in step 1 is dried at a room temperature of 25° C. for 12 h, and then is dried at 70° C. for 12 h, and finally is calcined at 600° C. for 4 h in air atmosphere to obtain the molybdenum-vanadium bimetal composite oxide supported on alumina is obtained, wherein the molecular formula thereof is $Mo_1V_y$, and y represents an amount of V corresponding to 1 mol of Mo, y=4, 6, 9, 12, 18, 30, i.e. the molar ratio of V to Mo.

Step 3: the $Mo_1V_y$ solid powder is pressed into a granular catalyst with a size of 20-40 mesh.

Embodiment 2

The reaction is performed by using the same method as in embodiment 1. The difference thereof is that the mass of ammonium molybdate in step 1 is 0, and the $VO_x$ catalyst is obtained.

Embodiment 3

Step 1, 1.472 parts by mass of ammonium molybdate (($NH_4)_6Mo_7O_{24} \cdot 4H_2O$) are weighed and dissolved in 3 mL of deionized water. 2.0 parts by mass of $Al_2O_3$ are impregnated in the above-mentioned solution, and are dried at a room temperature for 12 h and dried at 80° C. for 2 h.

Step 2, the product obtained in step 1 is dried at a room temperature of 25° C., and is dried at 70° C. for 12 h, and is finally calcined at 600° C. for 4 h in air atmosphere to obtain molybdenum oxide supported on alumina, wherein the molecular formula of molybdenum oxide is $MoO_x$.

Step 3, the $MoO_x$ solid powder is pressed into a granular catalyst with a size of 20-40 mesh.

Embodiment 4

0.25 g-0.8 g of the $VO_x$, $Mo_1V_y$, and $MoO_x$ oxygen supports (i.e., three kinds of oxide catalysts) obtained in embodiments 1-3 are respectively weighed and mixed with 2 mL of quartz sand (SiC), and are then added into a fixed bed tubular reactor. The experiment is performed at 450° C.-500° C. under a normal pressure condition. $N_2$ is introduced to remove oxygen and air, then propane is introduced, wherein the total flow of propane and nitrogen is 21 ml/min, and the volume percent of propane is 20%. The product compositions are detected by gas chromatography.

The conversion rate of propane is calculated according to the following formula:

$$X_{C_3H_6} = F_{C_3H_6}^{in} - F_{C_3H_6}^{out} / F_{C_3H_6}^{in},$$

wherein: $X_{C_3H_6}$—conversion rate of propane, %;
$F_{C_3H_6}^{in}$—molar flow of propane in reactor inlet, mol/min; and
$F_{C_3H_6}^{out}$—molar flow of propane in reactor outlet, mol/min.

The selectivity of the gas phase product is calculated according to the following formula:

$$S_{product\ A} = n_{product\ A} / \Sigma n_{product} = x_{product\ A}$$

wherein: $S_{product\ A}$—selectivity of gas phase product A, %;
$n_{product\ A}$—yield of gas phase product A, mol;
$\Sigma n_{product}$—sum of amounts of all product materials of gas phase, mol; and
$x_{product\ A}$—content of gas phase product A in all gas phase products.

The gas phase product A includes: $C_3H_6$, $CO_x$ (carbon oxide, i.e. carbon monoxide, carbon dioxide), $CH_4$, $C_2H_6$, and $C_2H_4$.

Figure 2:
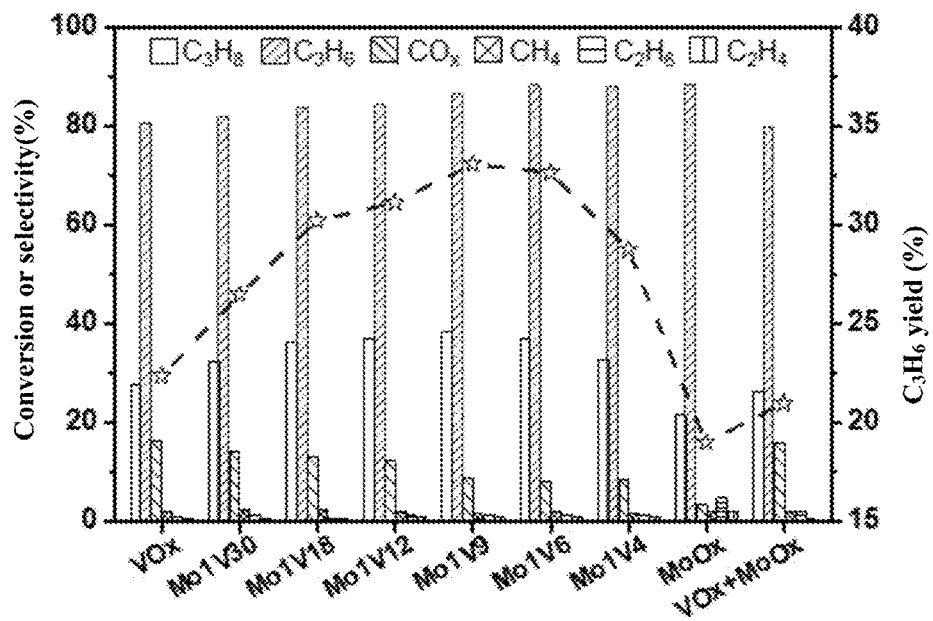
FIG. 2 is a schematic diagram showing a result of a catalyst activity test with different addition amounts of Mo in a chemical looping oxidative dehydrogenation process of propane.

The catalyst activity of the above embodiments is determined at a reaction time of 5 min. As shown in FIG. 2, the histogram represents the conversion rate or selectivity of the product, and the stars correspond to the propylene yields. With the increase of the molybdenum content, the conversion rate of propane is increased, and the selectivity of propylene is enhanced, which are both maintained above 80%. The highest selectivity for propylene of $Mo_1V_6$ is 89%. The pure vanadium oxide $VO_x$ has a relatively high surface oxygen activity, resulting in the complete oxidation of propane into $CO_x$. The pure molybdenum oxide $MoO_x$ has relatively low surface oxygen activity, resulting in a low conversion rate of propane, and propane or propylene is completely oxidized into $CO_x$ (compared with $VO_x$, $Mo_1V_y$, and the combination of $VO_x$ and $MoO_x$). The molybdenum-vanadium bimetal oxide can effectively enhance the selectivity for propylene while inhibiting the surface oxygen activity. However, an excessive addition of molybdenum leads to a decrease of the conversion rate of propane and the selectivity for propylene. Therefore, the optimum addition amount of Mo of the molybdenum-vanadium bimetal oxide is $Mo_1V_6$. (The products represented by the histogram in the drawings correspond to FIG. 2).

Figure 3:
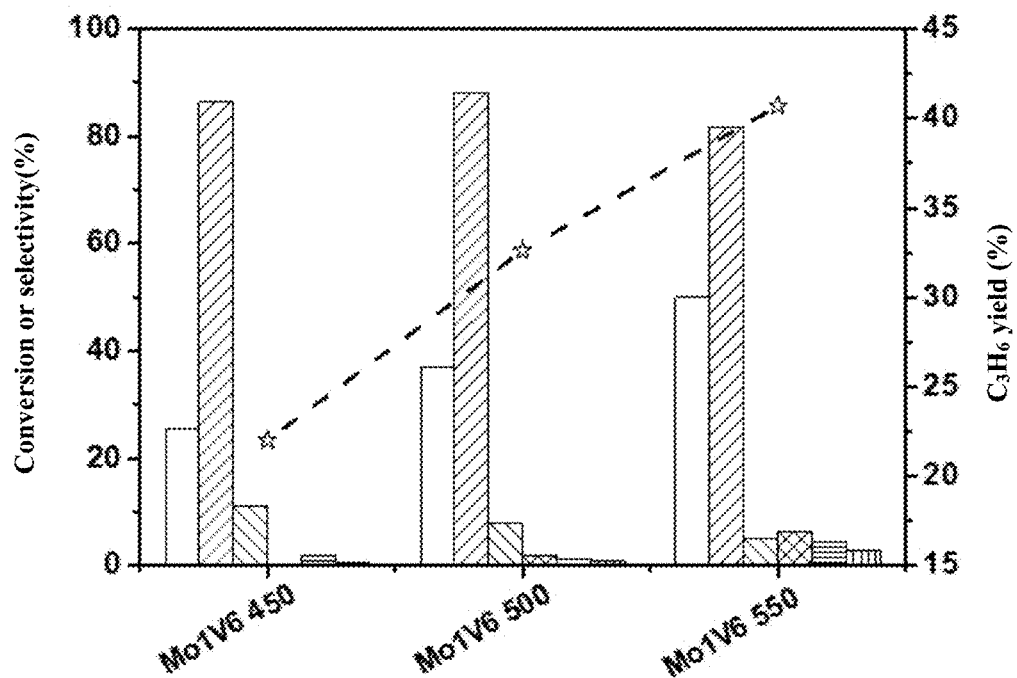
FIG. 3 is a schematic diagram showing a result of a catalyst activity test with different temperatures in a chemical looping oxidative dehydrogenation process of propane.
Figure 4:
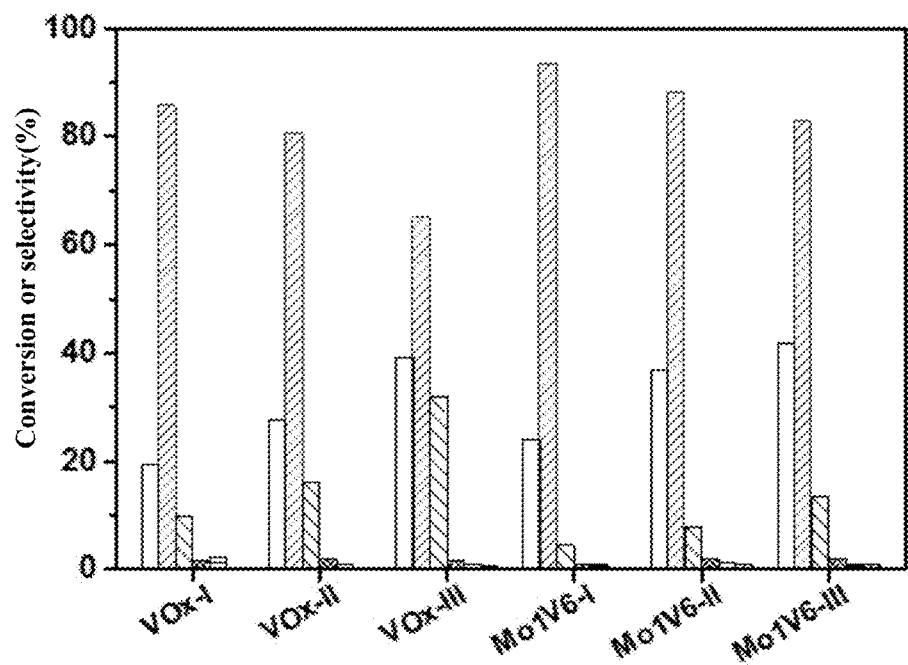
FIG. 4 is a schematic diagram showing a result of a catalyst activity test at different weight hourly space velocities (WHSV) in a chemical looping oxidative dehydrogenation process of propane.

Referring to the molybdenum-vanadium bimetal oxide $Mo_1V_6$ with an optimum addition amount of Mo, the results of the performance test of $Mo_1V_6$ with different reaction temperatures in FIG. 3 show that, as the reaction temperature increases, the conversion rate of propane increases, while the selectivity of $CO_x$ is gradually decreased. However, as the reaction temperature is further increased, the C—C bond of propane is more inclined to be broken to produce methane, resulting in a decrease in the selectivity for propylene. According to the schematic diagram showing the results of the catalyst activity tests at different weight hourly space velocities (WHSV) in the chemical looping oxidative dehydrogenation process of propane by using $VO_x$ and $Mo_1V_6$ in FIG. 4, where I, II and III correspond to the oxygen support of 0.25 g, 0.5 g and 0.8 g, respectively (the WHSV is a ratio of the gas flow to the mass of the catalyst, and the WHSV is adjusted by changing the mass of the catalyst with a constant gas flow), as the WHSV of the reaction decreases, the conversion rate of propane is increased, while the selectivity of propylene is reduced. The reason is that the decrease of residence time cause propane or propylene to be completely oxidized by an oxide with a strong surface activity to generate $CO_x$.

Figure 5:
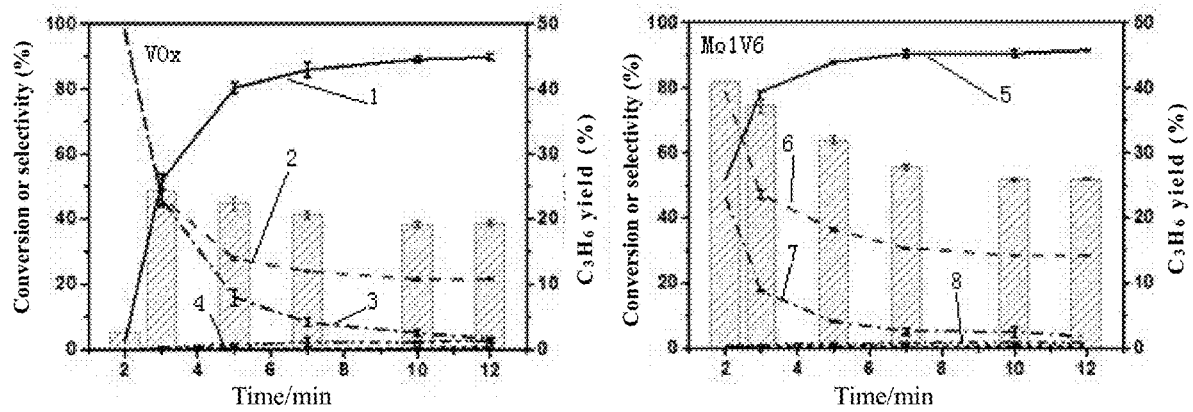
FIG. 5 shows schematic diagrams of results of catalyst activity tests by respectively using $VO_x$ catalyst and $Mo_1V_6$ catalyst with different reaction times in the chemical looping oxidative dehydrogenation process of propane.

FIG. 5 shows schematic diagrams of the results of catalyst activity tests by respectively using $VO_x$ catalyst and $Mo_1V_6$ catalyst at different reaction times in the chemical looping oxidative dehydrogenation process of propane. The histogram corresponds to the propylene yield, and the curves 1-4 correspond to the curve using the metal V oxide catalyst. Curve 1 presents the selectivity of propylene. Curve 2 presents the conversion rate of propane. Curve 3 presents the selectivity for carbon oxide. Curve 4 presents the selectivity for methane, ethane, and ethylene, and others. Curves 5-8 correspond to the curve using the molybdenum-vanadium bimetal catalyst. Curve 5 presents the selectivity for propylene. Curve 6 presents the conversion rate of propane. Curve 7 presents the selectivity for carbon oxide. Curve 8 presents the selectivity for methane, ethane, and ethylene, and others. As the reaction time increases, the lattice oxygen in the oxygen support is gradually consumed. According to the results of the activity tests at different reaction times in the chemical looping oxidative dehydrogenation process of propane by respectively using $VO_x$ catalyst and $Mo_1V_6$ catalyst in FIG. 5, in the initial stage 0-3 min of the reaction, the activity of lattice oxygen and the conversion rate of propane are the highest, while the higher oxygen activity leads to complete oxidation to generate $CO_x$. As the surface lattice oxygen is gradually consumed, the highest $C_3H_6$ yield is obtained at 3-5 min, which indicates that the bulk phase lattice oxygen is the main active oxygen species that activates propane to produce propylene. At the late stage of the reaction of 10-15 min, the lattice oxygen is exhausted. At this time, the main reaction is the non-oxidative dehydrogenation reaction of propane in $V_2O_3$.

Figure 6:
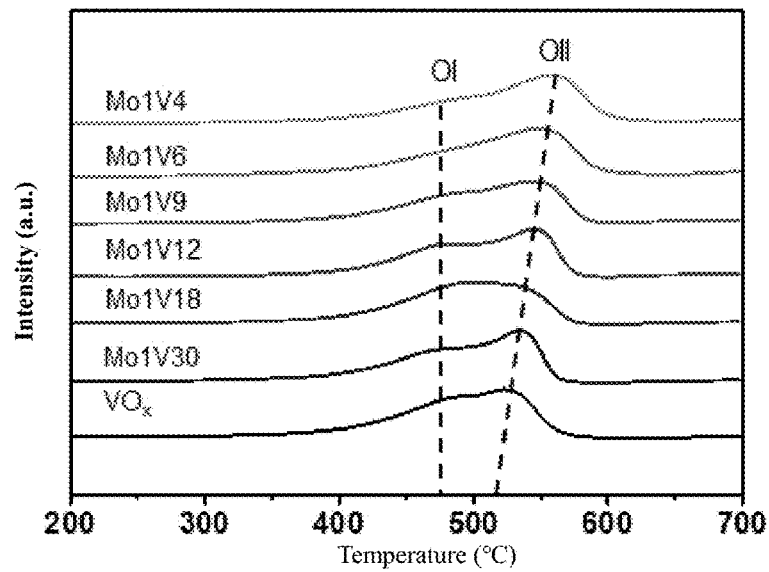
FIG. 6 is a spectrum diagram showing a result of a $H_2$ temperature-programmed reduction ($H_2$-TPR) test of a fresh oxygen support (catalyst) prepared by the present invention.
Figure 7:
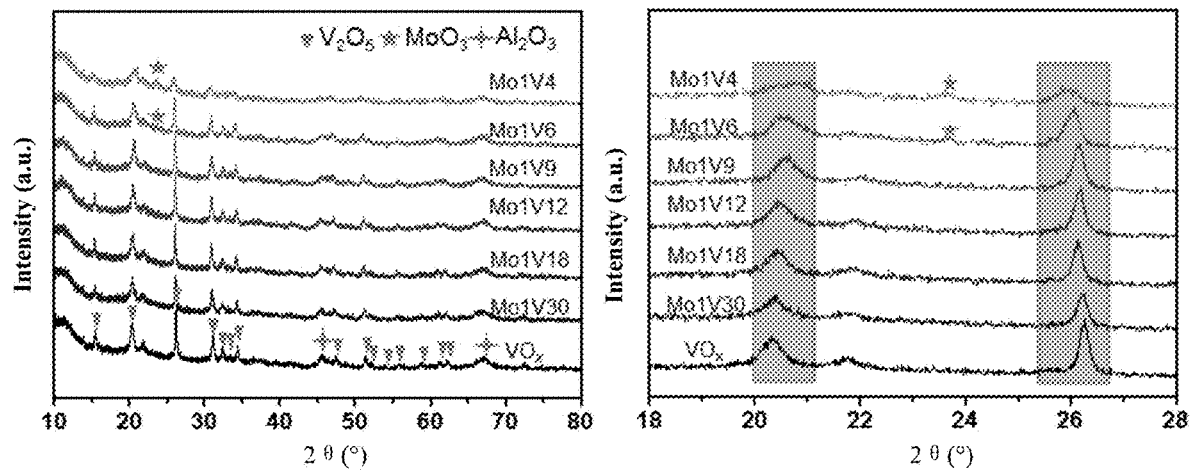
FIG. 7 is a spectrum diagram showing a result of a X-ray diffraction (XRD) test of a fresh oxygen support (catalyst) of the present invention.

The fresh oxygen support (catalyst) prepared in the present invention is performed on a $H_2$-TPR test, and the results are shown in FIG. 6. There are mainly two types of oxygen species in the oxygen support, i.e. OI and OIL The lattice oxygen OI releasing at a lower temperature has a higher activity, which belongs to the main oxygen species that completely oxidizes propane or propylene. The lattice oxygen OII releasing at a higher temperature has a moderate activity, and can selectively oxidatively dehydrogenate propane to produce propylene. In addition, with the increase of the Mo content, the reduction peak of the OI species gradually weakens, while the reduction peak of the OII species gradually increases, indicating that the addition of Mo effectively regulates the activity of the lattice oxygen species in the oxygen support, and inhibits the OI species having a stronger activity. The XRD experiment is performed on an X-ray diffractometer of model Rigaku C/mx-2500. As shown in FIG. 7, the fresh prepared catalyst mainly contains $V_2O_5$. With the addition of Mo content, the characteristic peak of $V_2O_5$ occurs a shift at a certain angle, which indicates that Mo enters the bulk phase lattice of $V_2O_5$, resulting in a lattice distortion of $V_2O_5$, and the lattice constant is changed, which provides an evidence for the formation of molybdenum-vanadium solid solution.

Figure 8:
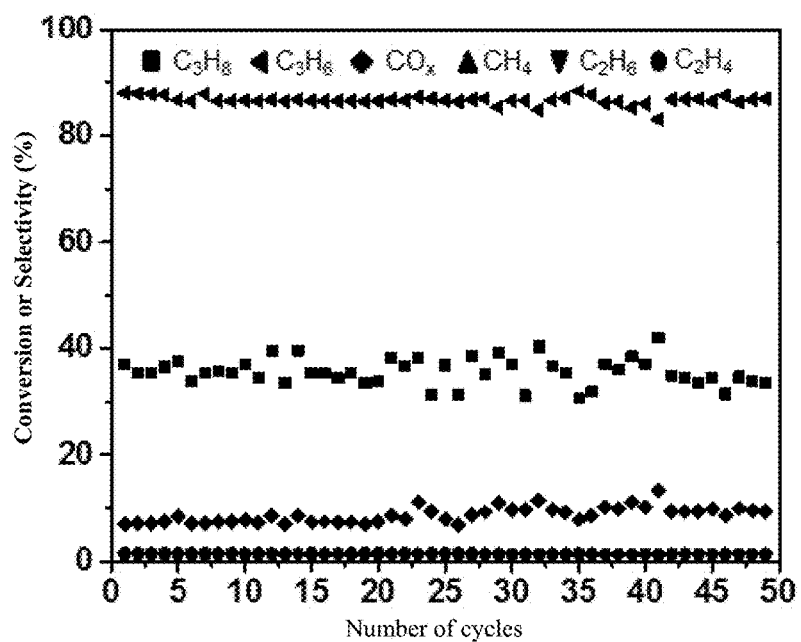
FIG. 8 shows schematic diagrams of results of cycling stability tests of a reaction regeneration cycle by using the catalyst $Mo_1V_6$ in a chemical looping oxidative dehydrogenation process of propane.
Figure 9:
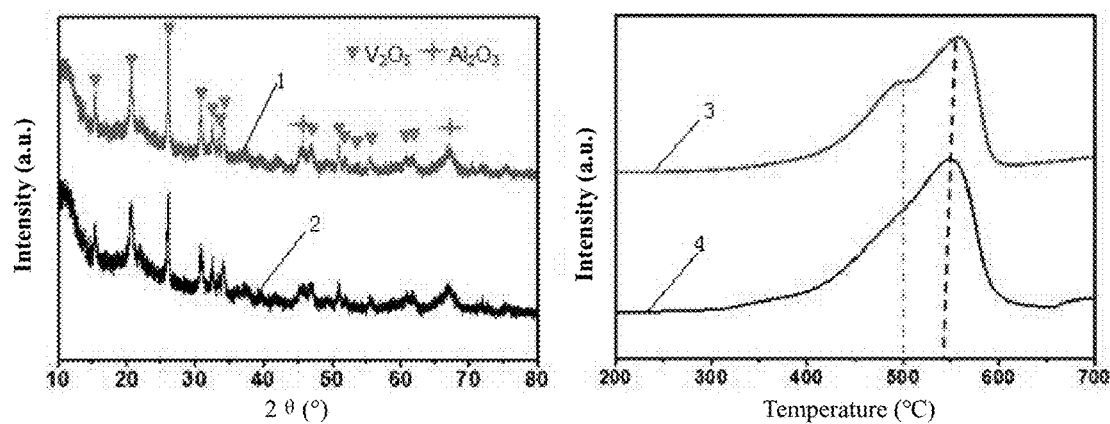
FIG. 9 shows schematic diagrams of results of cycling stability tests of a reaction regeneration cycle of the oxygen support by using the catalyst $Mo_1V_6$ before and after a chemical looping oxidative dehydrogenation process of propane.

After the reaction is completed, the lattice oxygen is gradually consumed, resulting in a decrease of the catalyst activity. The catalyst is regenerated (i.e., oxidized to a high-valence state) by using oxygen or air, and recovers lattice oxygen and returns back to the reactor for reaction. The result of the cycling stability test of the chemical looping oxidative dehydrogenation process of propane in FIG. 8 (each product corresponds to the mark in the drawing) shows that the performance basically remains unchanged during the redox cycle process, indicating that the molybdenum-vanadium bimetal oxide has a good oxidative regeneration performance. After 50 cycles (cycles of "reaction-regeneration-reaction-regeneration"), the results of XRD and $H_2$-TPR of the oxygen support and the fresh oxygen support are shown in FIG. 9, where the left side is XRD, and curves 1 and 2 represent XRD line spectra of the fresh support and the cycled oxygen support, respectively; and the right side is $H_2$-TPR, and the curves 3 and 4 represent the $H_2$-TPR line spectra of the fresh support and the cycled oxygen support, respectively. In contrast, it shows that the phase structure of the oxygen support is not changed substantially, which well confirms the excellent stability performance of the molybdenum-vanadium solid solution.

Figure 10:
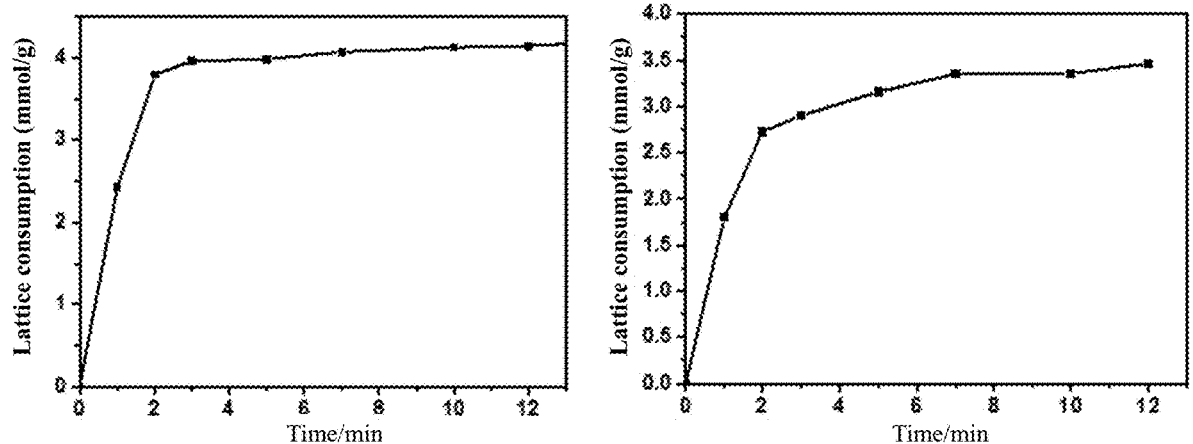
FIG. 10 shows schematic diagrams of results of lattice oxygen consumption of $VO_x$ and $MoV_6$ at different reaction times in the chemical looping oxidative dehydrogenation process of propane.
Figure 11:
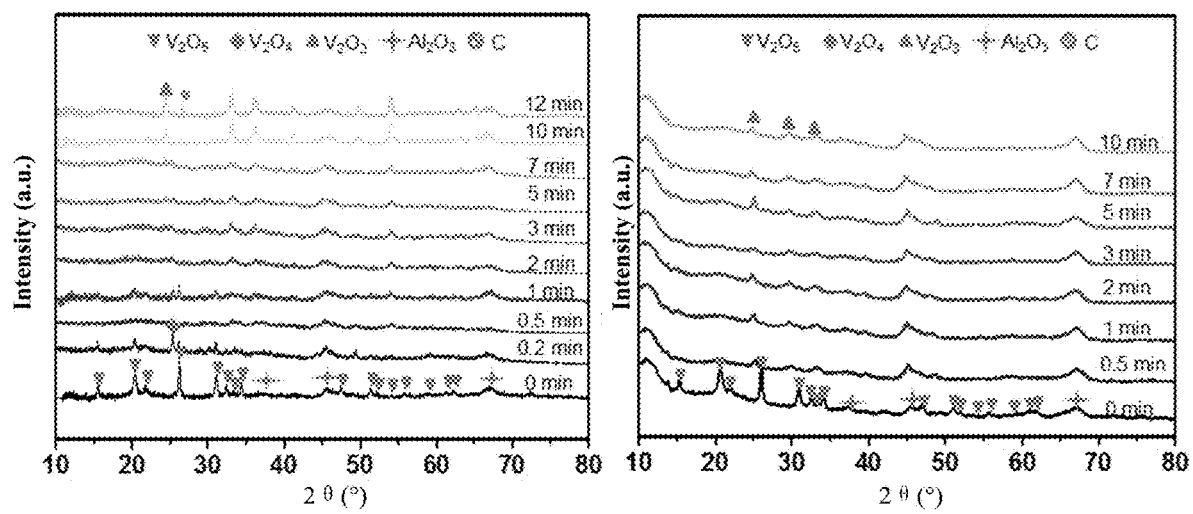
FIG. 11 shows schematic diagrams of phase changes of $VO_x$ and $Mo_1V_6$ at different reaction times in the chemical looping oxidative dehydrogenation process of propane.

The schematic diagrams in FIG. 10 and FIG. 11 showing results of lattice oxygen consumption tests and phase changes of $VO_x$ catalyst and $Mo_1V_6$ catalyst at different reaction times in the chemical looping oxidative dehydrogenation process of propane, where the left side presents the catalyst $VO_x$, and the right side presents the catalyst $Mo_1V_6$. With the increase of the reaction time, the lattice oxygen in the oxygen support is gradually consumed, and is remarkably consumed at the initial stage, in that propane and propylene are completely oxidized into $CO_x$, and the lattice oxygen is greatly consumed. However, with the consumption of lattice oxygen, the oxygen activity is constantly weakened. The lattice oxygen selectively oxidatively dehydrogenate propane to generate propylene. The lattice oxygen is consumed slowly, and is exhausted at the late stage, and then the reaction enters a non-oxidative dehydrogenation stage. According to the lattice oxygen consumption comparison of $VO_x$ and $Mo_1V_6$ in the left diagram, the addition of Mo effectively reduces a large amount of lattice oxygen consumed by the side reaction that generates $CO_x$ and increases the lattice oxygen consumed by the oxidative dehydrogenation that selectively produces propylene. With the increase of the reaction time, $VO_x$ and $Mo_1V_6$ undergo a change in the phase structure, from $V_2O_5$ to $V_2O_4$ to $V_2O_3$, which mainly correspond to the complete oxidation stage, the selective oxidative dehydrogenation stage and the non-oxidative dehydrogenation stage, respectively, in view of the reaction time.

The catalyst may be prepared according to an adjustment of the preparation parameters of the contents of the present disclosure, realizing an effective catalysis of propane. The illustrative description of the present disclosure is provided above. It should be noted that any simple variations, modifications or other equivalent replacements made by those skilled in the art without creative efforts should fall within the protection scope of the present disclosure.

We claim:

1. A method of chemical looping oxidative dehydrogenation of a light alkane over a molybdenum-vanadium bimetal oxide catalyst, comprising:

uniformly mixing a molybdenum-vanadium bimetal oxide catalyst with quartz sand in a reactor, wherein, the molybdenum-vanadium bimetal oxide catalyst comprises: a solid solution composed of an oxide of molybdenum (Mo) and an oxide of vanadium (V), a molar ratio of Mo and V in the molybdenum-vanadium bimetal oxide catalyst is 1-(4-30), and Mo enters bulk phase lattice of $V_2O_5$, resulting in a lattice distortion of $V_2O_5$ and forming the solid solution, and a mass ratio of the molybdenum-vanadium bimetal oxide catalyst to the quartz sand is (0.2-1):1;

introducing nitrogen to the reactor to remove oxygen and air, and then introducing a light alkane to the reactor, wherein, the light alkane is an alkane selected from the group consisting of ethane, propane, n-butane and iso-butane, a total flow of the light alkane and nitrogen is 20 ml/min-50 ml/min, and a volume percent of the light alkane to a total volume of the light alkane and the nitrogen is 10%-30%; and contacting the light alkane with the molybdenum-vanadium bimetal oxide catalyst at atmospheric pressure and a temperature from 450° C.-500° C. to produce a product comprising an alkene.

2. The method of chemical looping oxidative dehydrogenation of the light alkane according to claim 1, wherein, an oxidative dehydrogenation reaction is performed under an anaerobic condition, the molybdenum-vanadium bimetal oxide catalyst is used as an oxygen support, and reacts with the light alkane via the oxidative dehydrogenation reaction, lattice oxygen in the oxygen support reacts with a hydrogen atom in the light alkane to generate water, the oxygen support is reduced to a low-valence state, and the light alkane is oxidized to an alkene.

3. The method of chemical looping oxidative dehydrogenation of the light alkane according to claim 2, wherein, lattice oxygen in oxygen support participates in the oxidative dehydrogenation reaction, and as the oxidative dehydrogenation reaction proceeds, the lattice oxygen is gradually consumed and results in a decrease in an activity of the molybdenum-vanadium bimetal oxide catalyst and a low-valence state oxygen support; the low-valence state oxygen support is cycled and regenerated by reacting with air or oxygen to oxidize the low-valence state oxygen support to a high-valence state oxygen support and returning the high-valence state oxygen support to the reactor.

4. The method of chemical looping oxidative dehydrogenation of the light alkane according to claim 1, wherein, the contacting comprises a gas-solid contacting method selected from a gas-solid countercurrent contacting method and a gas-solid concurrent contacting method, and the reactor employed in the oxidative dehydrogenation reaction is one selected from the group consisting of a fixed bed reactor, a moving bed reactor, and a circulating fluidized bed reactor.

5. The method of chemical looping oxidative dehydrogenation of the light alkane according to claim 1, wherein, the mass ratio of the molybdenum-vanadium bimetal oxide catalyst to the quartz sand is (0.5-0.8):1.

6. The method of chemical looping oxidative dehydrogenation of the light alkane according to claim 1, wherein, the molar ratio of Mo and V in the molybdenum-vanadium bimetal oxide catalyst is 1:(6-18).

7. The method of chemical looping oxidative dehydrogenation of the light alkane according to claim 1, wherein, the molybdenum-vanadium bimetal oxide catalyst is a supported catalyst, a support is $Al_2O_3$, $TiO_2$, $SiO_2$ or a molecular sieve, a mass percent of the oxide of molybdenum over a mass of the support is 1%-30%, and a mass percent of the oxide of vanadium over the mass of the support is 4%-60%.

8. The method of chemical looping oxidative dehydrogenation of the light alkane according to claim 7, wherein, the mass percent of the oxide of molybdenum over the mass of the support is 10%-20% and the mass percent of the oxide of vanadium over the mass of the support is 40%-60%.

* * * * *